United States Patent [19]

Pauluth et al.

[11] Patent Number: 4,730,904
[45] Date of Patent: Mar. 15, 1988

[54] ORGANOSILICON COMPOUNDS

[75] Inventors: Detlef Pauluth, Darmstadt; Klaus Bofinger, Mühltal; Michael Römer, Rodgau; Bernhard Scheuble, Alsbach; Georg Weber, Erzhausen, all of Fed. Rep. of Germany

[73] Assignee: Merck Patent Gesellschaft mit beschrankter Haftung, Darmstadt, Fed. Rep. of Germany

[21] Appl. No.: 873,913

[22] Filed: Jun. 13, 1986

[30] Foreign Application Priority Data

Jun. 13, 1985 [DE] Fed. Rep. of Germany ....... 3521201
Jan. 22, 1986 [DE] Fed. Rep. of Germany ....... 3601742

[51] Int. Cl.$^4$ .................. C09K 19/56; C09K 19/54; G02F 1/13; C07F 7/04
[52] U.S. Cl. ................... 350/340; 252/299.4; 252/299.5; 428/1; 556/445; 556/448; 556/410; 556/414; 556/416; 556/417; 556/423
[58] Field of Search .......... 252/299.6, 299.63, 299.66, 252/299.4, 299.5, 299.01; 350/340, 341; 260/349; 556/410, 414, 416, 422, 445, 447, 417, 423, 448; 428/1

[56] References Cited

U.S. PATENT DOCUMENTS

| | | | |
|---|---|---|---|
| 3,719,650 | 3/1973 | Joy | 556/410 |
| 3,728,008 | 4/1973 | Allan et al. | 350/340 |
| 3,853,935 | 12/1974 | Roshdy et al. | 556/422 |
| 3,898,255 | 8/1975 | Meiller | 556/422 |
| 4,316,041 | 2/1982 | Totten et al. | 252/299.4 |
| 4,388,453 | 6/1983 | Finkelmann et al. | 252/299.4 |
| 4,490,015 | 12/1984 | Kawarada et al. | 350/340 |
| 4,645,844 | 2/1987 | Berger et al. | 556/445 |
| 4,678,283 | 7/1987 | Kreuzer et al. | 252/299.4 |

FOREIGN PATENT DOCUMENTS

| | | | |
|---|---|---|---|
| 173369 | 3/1986 | European Pat. Off. | 252/299.4 |
| 3331515 | 3/1985 | Fed. Rep. of Germany | 252/299.4 |
| 60-252486 | 12/1985 | Japan | 252/299.6 |
| 2066497 | 7/1981 | United Kingdom | 350/340 |

OTHER PUBLICATIONS

Bradshaw et al, J. Chromatography, 357, pp. 69–78 (1986).

Primary Examiner—Teddy S. Gron
Assistant Examiner—J. E. Thomas
Attorney, Agent, or Firm—Millen & White

[57] ABSTRACT

Organosilicon compounds of the formula I $$R^1-A^1-A^2-O-C_nH_{2n}-SiX_aY_bZ_c \qquad I$$

wherein $R^1$, $A^1$, $A^2$, X, Y, Z, n, a, b and c have the meaning given can be used for producing a homotropic orientation of liquid crystal phases on surfaces.

19 Claims, No Drawings

ORGANOSILICON COMPOUNDS

BACKGROUND OF THE INVENTION

The production of a uniform and stable homotropic orientation of liquid crystal phases was hitherto technologically quite difficult. Thus, the liquid crystal phase used was doped with surface-active substances, such as lecithins, long-chain aliphatic amines, quaternary ammonium or phosphonium salts or carboxylatochromium complexes (Appl. Phys. Lett 27, 268 (1975). Coating of glass surfaces with the substances mentioned before introduction of the liquid crystal phase was also customary. The uniformity and stability of the resulting homotropic orientation of the liquid crystal phases, however, leaves something to be desired.

Trisalkanolyoxysilanes for producing a homotropic orientation of liquid crystal phases on surfaces are known from German patent application No. P 33 31 515 (U.S. Ser. No. 647,210 of Sept. 4, 1984). However, these compounds have a number of disadvantages. Thus, dark brown by-products which cannot be separated off from the desired trisalkanolyoxysilane are frequently formed during their preparation from acid anhydrides and trichlorosilanes. Products contaminated in this manner are no longer suitable for surface treatment, since they reduce the optical transparency of the carrier material. Hydrolysis of the trisalkanolyoxy compounds on the carrier surface by the process described in No. P 33 31 515 furthermore frequently leads only to low molecular weight hydrolysis products which are volatile with the steam used and thus do not contribute to modification of the surface treated, which results in incomplete or only partial surface orientation of liquid crystal phases applied.

SUMMARY OF THE INVENTION

It is therefore an object of this invention to provide a better, in particular more uniform and more stable, homotropic orientation of liquid crystal phases on surfaces.

Upon further study of the specification and appended claims, further objects and advantages of this invention will become apparent to those skilled in the art.

These objects have been achieved by providing new organosilicon compounds of the formula I

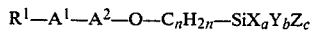

wherein
$R^1$ is H, an alkyl group of 1–10 C atoms, it also being possible for one or two non-adjacent $CH_2$ groups to be replaced by O atoms, F, Cl, Br or CN,
$A^1$ and $A^2$ are each 1,4-phenylene or 1,4-cyclohexylene groups, or one of the groups $A^1$ and $A^2$ is a single bond,
X, Y and Z are each H, F, Cl, Br, I, CN, NC, OCN, NCO, SCN, $N_3$ or an alkoxy group with 1 to 15 C atoms, it also being possible for one or more non-adjacent $CH_2$ groups to be replaced by —O—, —CO— —and/or —CH=CH—,
a, b and c are 0, 1, 2 or 3 and
n is 2, 3, 4, 5 or 6,
with the proviso that $a+b+c=3$ and at least one of the substituents is other than H.

The compounds of the formula I are excellently suitable for homotropic alignment of liquid crystal phases on surfaces, for example sheets of glass, which can also be coated, such as are used in the production of electrooptical display elements. Because of their negative dielectric anisotropy, liquid crystal phases orientated in this manner can be influenced in their alignment by an external electrical field. They are suitable for use in displays which are operated in accordance with the principle of deformation of aligned phases (Appl. Phys. Lett. 19, 391 (1971)), the principle of dynamic scattering (Proc.IEEE 56, 1162 (1968)) or in accordance with the guest-host principle (Mol. Cryst. Liq. Cryst. 63, 19 (1981)).

These objects have also been achieved by providing a process for the preparation of these compounds, characterized in that an unsaturated compound of the formula II

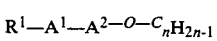

is reacted with a silane $H-SiX_aY_bZ_c$, wherein $R^1$, $A^1$, $A^2$, X, Y, Z, a, b, c and n have the meaning given above or in that a halide of the formula IV

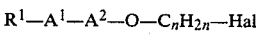

is reacted with a silane $H-SiX_aY_bZ_c$, wherein $R^1$, $A^1$, $A^2$, X, Y, Z, a, b, c and n have the meaning given above and Hal is Cl, Br or I, or in that a silicon compound of the formula I in which at least one of the substituents X, Y and Z is H, Cl, Br or I, is reacted with an alkali metal, alkaline earth metal or silver salt of the anions $CN^-$, $NC^-$, $OCN^-$, $NCO^-$, $SCN^-$, $NCS^-$, or $N_3^-$, or with their associated acids HCN, HOCN, HNCO, HSCN, HNCS or $HN_3$ or, for the preparation of isocyanates, with urea, or of isothiocyanates, with thiourea, or in that a halogenosilane of the formula I wherein at least one of the radicals X, Y and Z is Cl, Br and/or I and $R^1$, $A^1$, $A^2$, a, b, c and n have the meaning given above, is reacted with a compound containing hydroxyl groups.

The invention furthermore relates to the use of the compounds of the formula I as components of liquid crystal dielectrics for electrooptical display elements and to their use for producing a homotropic orientation of liquid crystal phases on surfaces, inter alia in printing processes. The invention furthermore relates to liquid crystal dielectrics containing at least one compound of the formula I and to electrooptical display elements which contain such dielectrics and/or contain surfaces which have been treated with a compound of the formula I. Methods for producing a homeotropic orientation of liquid crystals on surfaces are known from, e.g., Uchida et al., Ipn. J. Appl. Phys. 11 (1972) 1559; Kahn et al., Proc. IEEE 61 (1973) 823; Wolff et al., Mol. Cryst. Liq.Cryst. 23 (1973) 187.

Above and below, $R^1$, $R^2$, $A^1$, $A^2$ and n have the meaning given, unless expressly indicated otherwise.

According to the definition of groups $A^1$ and $A^2$, the compounds of the formula I include those of the part formulae Ia to Id:

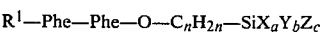     Ia

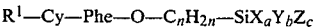     Ib

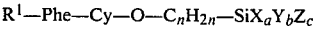     Ic

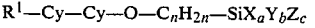     Id

In these formulae, Phe is 1,4-phenylene and Cy is 1,4-cyclohexylene. Compounds of the formulae Ia and Ib are preferred.

In the compounds of the formulae above and below, $R^1$ is preferably alkyl, or furthermore alkoxy (especially if this radical is on the Phe group) or another oxaalkyl group.

In the compounds of the formulae above and below, X, Y and Z are preferably identical (a=b=c=1) and are preferably halogen or alkoxy with 1 to 15 C atoms, in particular chlorine, methoxy, ethoxy, propyloxy, isopropyloxy or 1-methyl-3-oxobut-1-enyloxy.

The parameter n preferably has the value 3. The radical $C_nH_{2n}$ is preferably straight-chain and accordingly is, in particular, —$(CH_2)_3$—, or furthermore, in particular, —$(CH_2)_2$—, —$(CH_2)_4$—, —$(CH_2)_5$— or —$(CH_2)_6$—.

In the compounds of the formulae above and below, the alkyl portions can be straight-chain or branched. Preferably, they are straight-chain, have 1, 2, 3, 4, 5, 6 or 7 C atoms and accordingly are preferably methyl, ethyl, propyl, butyl, pentyl, hexyl or heptyl. $R^1$ can also be an alkyl group, it being possible for one ("alkoxy" or "oxaalkyl") or 2 ("alkoxyalkoxy" or "dioxaalkyl") non-adjacent $CH_2$ groups to be replaced by O atoms, and is preferably methoxy, ethoxy, propoxy, butoxy, pentoxy, hexoxy, heptoxy, 2-oxapropyl (=methoxymethyl), 2-oxabutyl (=ethoxymethyl) or 3-oxabutyl (=3-methoxyethyl) or 2-, 3-, 4-, 5- or 6-oxaheptyl.

$R^1$ can furthermore be, for example, octyl, nonyl, decyl, octoxy, nonoxy, decoxy, 2-, 3-, 4- , 5- , 6- or 7-oxaoctyl, 2-, 3-, 4-, 5-, 6-, 7- or 8-oxanonyl, 2-, 3-, 4-, 5-, 6-, 7-, 8- or 9-oxadecyl, or 1,3-dioxabutyl (=methoxymethoxy), 1,3-, 1,4- or 2,4-dioxapentyl, 1,3- 1,4-, 1,5- 2,4-, 2,5- or 3,5-dioxahexyl or 1,3-, 1,4-, 1,5-, 1,6-, 2,4-, 2,5-, 2,6-, 3,5-, 3,6- or 4,6-dioxaheptyl. Preferred meanings of the radical $R^1$ are furthermore F, Cl, Br or CN.

All of the groups mentioned for $R^1$ are also possible for X, Y and Z as are the corresponding groups wherein a mentioned O-atom is replaced by —CO— or —CH=CH—, inter alia. In the X/Y/Z alkoxy groups, typically up to 2 non-adjacent $CH_2$ groups can be replaced as described.

Compounds of the formulae I and Ia to Id with a branched radical $R^1$ may occasionally be of importance because of a better solubility in the usual liquid crystal base materials, and furthermore also as doping substance, if they are optically active. Branched groups of this type as a rule contain not more than one chain branching. Preferred branched radicals $R^1$ are isopropyl, 2-butyl (=1 methylpropyl), isobutyl (=2-methylpropyl), 2-methylbutyl or isopentyl (=3-methylbutyl); $R^1$ can furthermore denote 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 1-methylhexoxy, 1-methylheptoxy, 2-ethylhexoxy, 2-oxa-3-methylbutyl or 3-oxa-4-methylpentyl.

If the groups $A^1$ and/or $A^2$ are cyclohexylene groups disubstituted in the 1- and 4-position, the substituents can be in the cis-or trans-position. Compounds with the trans-configuration are preferred.

Compounds of the formula I with optically active C atoms include both the racemates and the corresponding optically active enantiomers, as well as mixtures thereof.

The compounds of the formula I can be prepared by methods which are known per se, such as are described in the literature (for example in the standard works, such as Houben-Weyl, Methoden der Organischen Chemie (Methods of Organic Chemistry), Volume XIII, 5, George-Thieme-Verlag, Stuttgart), and in particular under reaction conditions which are known and suitable for the reactions mentioned. Variants which are known per se and are not mentioned here in more detail can furthermore also be used.

They can be prepared, for example, by reacting an unsaturated ether of the formula II $$R^1—A^1—A^2—OC_nH_{2n-1} \qquad II$$

with a silane $H—SiX_aY_bZ_c$, wherein $R^1$, $A^1$, $A^2$, X, Y, Z, a, b, c and n have the meaning given above.

The silanes of the formula $H—SiX_aY_bZ_c$ are known or can be prepared by known methods such as are described, for example, in the above literature.

The ethers of the formula II can in turn be prepared by alkenylation of hydroxy compounds of the formula $$R^1—A^1—A^2—OH \qquad III$$

with a corresponding alkenyl halide of the formulae $C_nH_{2n-1}$ Cl or $C_nH_{2n-1}$ Br or an alkenyl sulfonate of the formula alkyl—$SO_2$—$C_nH_{2n-1}$ or aryl—$SO_2$—$C_nH_{2n-1}$.

The addition of the silanes $H—SiX_aY_bZ_c$ onto the unsaturated ethers of the formula II is advantageously carried out in the presence of an inert solvent, for example a halogenated hydrocarbon, such as methylene chloride at temperatures between about 0° and about 100°, advantageously at the boiling point. The silane is advantageously employed in an excess. The addition of a noble metal catalyst, for example a solution of $H_2PtCl_6$ in isopropanol, is advantageous in this process. The reaction can also be accelerated by addition of peroxides, such as diacetyl peroxide, and/or irradiation with light.

Silanes of the formula $H—SiX_aY_bZ_c$ can furthermore also be reacted with a halide of the formula IV $$R^1—A^1—A^2—O—C_nH_{2n}—Hal \qquad IV$$

wherein $R^1$, $A^1$, $A^2$, X, Y, Z, a, b, c and n have the meaning given above and Hal is Cl, Br or I. The reaction of the silanes with the halides of the formula IV is advantageously carried out in the presence of an inert solvent, such as, for example, an ether or a hydrocarbon, such as benzene or toluene. A base, for example in the form of an organic amine, such as pyridine, triethylamine or butylamine, is preferably added to the reaction mixture to remove the hydrogen halide formed. The reaction temperatures are between about 0° and about 150°, and are advantageously at the boiling point.

Silicon compounds of the formula I in which at least one of the substitutents X, Y and Z is H, Cl, Br or I, can furthermore be reacted with an alkali metal, alkaline earth metal or silver salt of the anions $CN^-$, $NC^-$, $OCN^-$, $NCO^-$, $SCN^-$, $NCS^-$ or $N_3^-$ or with their associated acids HCN, HOCS, HCNO, HSCN or $HN_3$ or, for the preparation of isocyanates, with urea or, if isothiocyanates, with thiourea.

The reaction of the alkali metal, alkaline earth metal or silver salts with the silanes of the formula I is advantageously carried out in an inert solvent, such as tetrahydrofuran or pyridine, at temperatures between about 0° and about 150°. The reaction is particularly advantageously carried out in salt melts of, for example, lithium chloride, potassium chloride and/or zinc chloride at temperatures from about 100° to about 500°, in particular between 150° and 350° C.

Silicon compounds of the formula I can furthermore be prepared from halogenosilanes of the formula I, wherein at least one of the radicals X, Y and Z is Cl, Br or I and $R^1$, $A^1$, $A^2$, a, b, c and n have the meaning given above, by reaction with a compound containing hydroxyl groups. Thus, the hydroxy compounds can be used per se or in the form of their salts, such as, for example, the alkali metal or alkaline earth metal salts, in the reaction with the halogenosilanes. In addition to primary, secondary and tertiary alcohols, enolizable 1,3-diketones or salts and reactive derivatives thereof, for example, are also suitable for reaction with halogenosilanes to give the organosilicon compounds according to the invention.

The reaction of the halogenosilanes of the formula I with the compounds containing hydroxyl groups is advantageously carried out in the presence of an inert solvent, such as, for example, an ether or a hydrocarbon, such as benzene or toluene. A base, for example in the form of an organic amine, such as pyridine, triethylamine or butylamine, is preferably added to the reaction mixture to remove the hydrogen halide formed. The reaction temperatures are between about −20° and 120°, and are advantageously at room temperature. The starting materials discussed above are all known and/or readily preparable from known starting materials.

The compounds of the formula I can be used directly for coating the surfaces to be treated. Oxidic surfaces, for example those of metal oxides, semi-metal oxides or non-metal oxides, but above all glass surfaces, are particularly suitable for coating.

Coating is advantageously carried out by a procedure in which the previously purified surfaces are wetted with an approximately 0.1 to 1% solution of a compound of the formula I in an inert solvent, for example a halogenated hydrocarbon, such as methylene chloride or 1,1,1-trichloroethane, and the solvent is evaporated in air. Heating or steam after-treatment of the surface thus modified, as with the compounds claimed in German Offenlegungsschrift No. 3,331,515, is generally not necessary with the compounds of the formula I. A uniform, high molecular weight film which is capable of homotropic orientation of liquid crystal phases is formed. To facilitate the handling of the compounds of the formula I, these can be dissolved in a suitable inert solvent, such as, for example, 1,1,1-trichloroethane, immediately after their preparation and after removal of volatile reaction components by distillation, and the solution can be stored in a bottle closed with a septum. Only the particular amount required is removed from the stock bottle with a syringe, so that the remainder of the solution remains protected from hydrolysis by atomspheric moisture.

For use in printing processes in which the use of polar solvents is required, the reaction of the halogenosilanes of the formula I can take place in an excess of the alcohol in question. The resulting solutions of organosilicon compounds of the formula I can then be used directly for surface coating, if appropriate after removal of the salt, formed during the reaction, of the organic base added. Methods which uniformly coat the surfaces to be treated, preferably screen printing techniques, are particularly suitable for coating by printing processes.

The compounds of the formula I thus provide an effective agent for producing a homotropic orientation of liquid crystal phases on surfaces.

It is also possible, however, to add one or more compounds of the formula I as doping substances to liquid crystal dielectrics, these dielectrics containing about 0.01 to 1, preferably about 0.05 to 0.5%, of compounds of formula I. Doping liquid crystal dielectrics with compounds of the formula I favorably effects the homotropic orientation of liquid crystal phases on surfaces.

The dielectrics according to this aspect of the invention comprise 2 to 25, preferably 3 to 15, components, at least one of which is a compound of the formula I. The other constituents are preferably selected from the nematic or nematogenic substances, in particular the known substances, from the classes of azoxybenzenes, benzylideneanilines, biphenyls, terphenyls, phenyl or cyclohexylbenzoates, cyclohexanecarboxylic acid phenyl or cyclohexyl esters, phenylcyclohexanes, cyclohexylbiphenyls, cyclohexylcyclohexanes, cyclohexylnaphthalenes, 1,4-bis-cyclohexylbenzenes, 4,4'-biscyclohexylbiphenyls, phenyl- or cyclohexylpyrimidines, phenyl- or cyclohexyldioxanes, phenyl- or cyclohexyldithianes, 1,2-bis-cyclohexylethanes, 1,2-bis-phenylethanes, 1-cyclohexyl-2-phenylethanes, optionally halogenated stilbenes, benzyl phenyl ethers, tolanes and substituted cinnamic acids.

The most important compounds which are suitable as constituents of such liquid crystal dielectrics can be characterized by the formula V

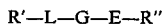    R'—L—G—E—R''    V wherein L and E are each a carbo- or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

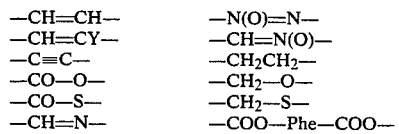

or a C—C single bond, Y is halogen, preferably chlorine or —CN and R' and R'' are alkyl, alkoxy, alkanoyloxy or alkoxycarbonyloxy. with up to 18, preferably up to 8, carbon atoms, or one of these radicals is also CN, NC, $NO_2$, $CF_3$, F, Cl or Br. The benzene and cyclohexane rings can also be substituted by F, Cl, —CN or —$CH_3$. In most of these compounds, R' and R'' differ from one another, one of these radicals usually being an alkyl or alkoxy group. However, other variants of the substituents envisaged are also customary. Many such substances or also mixtures thereof are commercially available.

The dielectrics according to the invention are prepared in a manner which is customary per se. As a rule, the components are dissolved in one another, advantageously at elevated temperature.

The liquid crystal dielectrics according to the invention can be modified by suitable additives so that they can be used in all the types of liquid crystal display elements known to date. Such additives are known to the expert and are described in detail in the literature. It is possible to add, for example, conductive salts, preferably ethyl-dimethyl-dodecylammonium 4-hexyloxybenzoate, tetrabutylammonium tetraphenylboranate or complex salts of crown ethers (compare, for example, I. Haller et al., Mol. Cryst. Liq. Volume 24, pages 249-258 (1973), to improve the conductivity, dichroic dyestuffs to produce colored guest/host systems or substances for modifying the dielectric anisotropy, the viscosity and/or the orientation of the nematic phases. Such substances are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

20 g of dichlorosilane are dissolved in 30 ml of methylene chloride at −20° C. A solution of 25.8 g of 3-(p-trans-4-propylcyclohexylphenoxy)-propene (m. 25°-28°, obtainable by reaction of Na p-trans-4-propylcyclohexylphenolate with allyl bromide) in 20 ml of methylene chloride and 0.2 ml of a 0.1 molar solution of hexachloroplatinic (IV) acid in isopropanol is added to the solution. The mixture is stirred under reflux for two days and the solvent and excess dichlorosilane are then distilled off. The residue, which consists of 1-dichlorosilyl-3-(p-trans-4-propylcyclohexylphenoxy)-propane is used for surface treatment in a 0.1 to 1% solution in 1,1,1-trichloroethane.

The following compounds are obtained analogously:
1-dichlorosilyl-3-p-cyclohexylphenoxy-propane
1-dichlorosilyl-3-(p-trans-4-methylcyclohexylphenoxy)-propane
1-dichlorosilyl-3-(p-trans-4-ethylcyclohexylphenoxy)-propane
1-dichlorosilyl-3-(p-trans-4-butylcyclohexylphenoxy)-propane
1-dichlorosilyl-3-(p-trans-4-isobutylcyclohexylphenoxy)-propane
1-dichlorosilyl-3-(p-trans-4-sec-butylcyclohexylphenoxy)-propane
1-dichlorosilyl-3-(p-trans-4-pentylcyclohexylphenoxy)-propane
1-dichlorosilyl-3-(p-trans-4-hexylcyclohexylphenoxy)-propane
1-dichlorosilyl-3-(p-trans-4-heptylcyclohexylphenoxy)-propane
1-dichlorosilyl-3-(p-trans-4-octylcyclohexylphenoxy)-propane
1-dichlorosilyl-3-(p-trans-4-nonylcyclohexylphenoxy)-propane
1-dichlorosilyl-3-(p-trans-4-decylcyclohexylphenoxy)-propane
1-dichlorosilyl-3-pbiphenyloxypropane
1-dichlorosilyl-3-(4'-methyl-biphenylyl-4-oxy)-propane
1-dichlorosilyl-3-(4'-ethyl-biphenylyl-4-oxy)-propane
1-dichlorosilyl-3-(4'-propyl-biphenylyl-4-oxy)-propane
1-dichlorosilyl-3-(4'-butyl-biphenylyl-4-oxy)-propane
1-dichlorosilyl-3-(4'-pentyl-biphenylyl-4-oxy)-propane
1-dichlorosilyl-3-(4'-hexyl-biphenylyl-4-oxy)-propane
1-dichlorosilyl-3-(4'-heptyl-biphenylyl-4-oxy)-propane
1-dichlorosilyl-3-(4'-octyl-biphenylyl-4-oxy)-propane
1-dichlorosilyl-3-(4'-nonyl-biphenylyl-4-oxy)-propane
1-dichlorosilyl-3-(4'-decyl-biphenylyl-4-oxy)-propane
1-dichlorosilyl-3-(4'-methoxy-biphenylyl-4-oxy)-propane
1-dichlorosilyl-3-(4'-ethoxy-biphenylyl-4-oxy)-propane
1-dichlorosilyl-3-(4'-propoxy-biphenylyl-4-oxy)-propane
1-dichlorosilyl-3-(4'-butoxy-biphenylyl-4-oxy)-propane
1-dichlorosilyl-3-(4'-pentoxy-biphenylyl-4-oxy)-propane
1-dichlorosilyl-3-(4'-hexoxy-biphenylyl-4-oxy)-propane
1-dichlorosilyl-3-(4'-heptoxy-biphenylyl-4-oxy)-propane
1-dichlorosilyl-3-(4'-methoxymethyl-biphenylyl-4-oxy)-propane
1-dichlorosilyl-3-(4'-methoxymethoxy-biphenylyl-4-oxy)-propane
1-dichlorosilyl-3-(4'-fluoro-biphenylyl-4-oxy)-propane
1-dichlorosilyl-3-(4'-chloro-biphenylyl-4-oxy)-propane
1-dichlorosilyl-3-(4'-bromo-biphenylyl-4-oxy)-propane
1-dichlorosilyl-3-(4'-cyano-biphenylyl-4-oxy)-propane
1-dichlorosilyl-3-(trans-4-phenylcyclohexoxy)-propane
1-dichlorosilyl-3-(trans-4-p-tolylcyclohexoxy)-propane
1-dichlorosilyl-3-(trans-4-p-ethylphenylcyclohexoxy)-propane
1-dichlorosilyl-3-(trans-4-p-propylphenylcyclohexoxy)-propane
1-dichlorosilyl-3-(trans-4-p-butylphenylcyclohexoxy)-propane
1-dichlorosilyl-3-(trans-4-p-pentylphenylcyclohexoxy)-propane
1-dichlorosilyl-3-(trans-4-p-hexylphenylcyclohexoxy)-propane
1-dichlorosilyl-3-(trans-4-p-heptylphenylcyclohexoxy)-propane
1-dichlorosilyl-3-(trans-4-p-methoxyphenylcyclohexoxy)-propane
1-dichlorosilyl-3-(trans-4-p-ethoxyphenylcyclohexoxy)-propane
1-dichlorosilyl-3-(trans-4-p-propoxyphenylcyclohexoxy)-propane
1-dichlorosilyl-3-(trans-4-p-butoxyphenylcyclohexoxy)-propane
1-dichlorosilyl-3-(trans-4-p-pentoxyphenylcyclohexoxy)-propane
1-dichlorosilyl-3-(trans-4-p-fluorophenylcyclohexoxy)-propane
1-dichlorosilyl-3-(trans-4-p-chlorophenylcyclohexoxy)-propane
1-dichlorosilyl-3-(trans-4-p-bromophenylcyclohexoxy)-propane
1-dichlorosilyl-3-(trans-4-p-cyanophenylcyclohexoxy)-propane
1-dichlorosilyl-3-(trans-4-(trans-4-propylcyclohexyl)cyclohexoxy)-propane
1-dichlorosilyl-3-(trans-4-(trans-4-butylcyclohexyl)cyclohexoxy)-propane
1-dichlorosilyl-3-(trans-4-(trans-4-pentylcyclohexyl)cyclohexoxy)-propane
1-dichlorosilyl-3-(trans-4-(trans-4-hexylcyclohexyl)cyclohexoxy)-propane
1-dichlorosilyl-3-(trans-4-(trans-4-heptylcyclohexyl)cyclohexoxy)-propane 1-dichlorosilyl-4-(p-trans-4-propylcyclohexylphenoxy)-butane
1-dichlorosilyl-5-(p-trans-4-propylcyclohexylphenoxy)-pentane
1-dichLorosilyl-6-(p-trans-4-propylcyclohexylphenoxy)-hexane
1-dichlorosilyl-2-methyl-3-(p-trans-4-propylcyclohexyl-phenoxy)-propane.

EXAMPLE 2

19.9 ml of tribromosilane and 0.2 ml of a 0.1 molar solution of hexachloroplatinic(IV) acid in isopropanol are added to a solution of 25.8 g of 3-(p-trans-4-propyl-cyclohexyl-phenoxy)-propene in 50 ml of methylene chloride. The mixture is stirred under reflux for two days and the solvent and excess tribromosilane are then distilled off. Crude 1-tribromosily-l3-(p-trans-4-propyl-cyclohexylphenoxy)-propane thus obtained is used for surface treatment in a 0.1 to 1% solution in 1,1,1-tri chloroethane.

The following compounds are obtained analogously:
1-tribromosilyl-3-p-cyclohexylphenoxy-propane
1-tribromosilyl-3-(p-trans-4-methylcyclohexylphenoxy)-propane
1-tribromosilyl-3-(p-trans-4-ethylcyclohexylphenoxy)-propane
1-tribromosilyl-3-(p-trans-4-butylcyclohexylphenoxy)-propane
1-tribromosilyl-3-(p-trans-4-isobutylcyclohexylphenoxy)-propane
1-tribromosilyl-3-(p-trans-4-sec.-butylcyclohexyl-phenoxy)-propane
1-tribromosilyl-3-(p-trans-4-pentylcyclohexylphenoxy)-propane
1-tribromosilyl-3-(p-trans-4-hexylcyclohexylphenoxy)-propane
1-tribromosilyl-3-(p-trans-4-heptylcyclohexylphenoxy)-propane
1-tribromosilyl-3-(p-trans-4-octylcyclohexylphenoxy)-propane
1-tribromosilyl-3-(p-trans-4-nonylcyclohexylphenoxy)-propane
1-tribromosilyl-3-(p-trans-4-decylcyclohexylphenoxy)-propane
1-tribromosilyl-3-p-biphenyloxy-propane
1-tribromosilyl-3-(4'-methyl-biphenylyl-4-oxy)-propane
1-tribromosilyl-3-(4'-ethyl-biphenylyl-4-oxy)-propane
1-tribromosilyl-3-(4'-propyl-biphenylyl-4-oxy)-propane
1-tribromosilyl-3-(4'-butyl-biphenylyl-4-oxy)-propane
1-tribromosilyl-3-(4'-pentyl-biphenylyl-4-oxy)-propane
1-tribromosilyl-3-(4'-hexyl-biphenylyl-4-oxy)-propane
1-tribromosilyl-3-(4'-heptyl-biphenylyl-4-oxy)-propane
1-tribromosilyl-3-(4'-octyl-biphenylyl-4-oxy)-propane
1-tribromosilyl-3-(4'-nonyl-biphenylyl-4-oxy)-propane
1-tribromosilyl-3-(4'-decyl-biphenylyl-4-oxy)-propane
1-tribromosilyl-3-(4'-methoxy-biphenylyl-4-oxy)-propane
1-tribromosilyl-3-(4'-ethoxy-biphenylyl-4-oxy)-propane
1-tribromosilyl-3-(4'-propoxy-biphenylyl-4-oxy)-propane
1-tribromosilyl-3-(4'-butoxy-biphenylyl-4-oxy)-propane
1-tribromosilyl-3-(4'-pentoxy-biphenylyl-4-oxy)-propane
1-tribromosilyl-3-(4'-hexoxy-biphenylyl-4-oxy)-propane
1-tribromosilyl-3-(4'-heptoxy-biphenylyl-4-oxy)-propane
1-tribromosilyl-3-(4'-methoxymethyl-biphenylyl-4-oxy)-propane
1-tribromosilyl-3-(4'-methoxymethoxy-biphenylyl-4-oxy)-propane
1-tribromosilyl-3-(4'-fluoro-biphenylyl-4-oxy)-propane
1-tribromosilyl-3-(4'-chloro-biphenylyl-4-oxy)-propane
1-tribromosilyl-3-(4'-bromo-biphenylyl-4-oxy)-propane
1-tribromosilyl-3-(4'-cyano-biphenylyl-4-oxy)-propane
1-tribromosilyl-3-(trans-4-phenylcyclohexoxy)-propane
1-tribromosilyl-3-(trans-4-p-tolylcyclohexoxy)-propane
1-tribromosilyl-3-(trans-4-p-ethylphenylcyclohexoxy)-propane
1-tribromosilyl-3-(trans-4-p-propylphenylcyclohexoxy)-propane
1-tribromosilyl-3-(trans-4-p-butylphenylcyclohexoxy)-propane
1-tribromosilyl-3-(trans-4-p-pentylphenylcyclohexoxy)-propane
1-tribromosilyl-3-(trans-4-p-hexylphenylcyclohexoxy)-propane
1-tribromosilyl-3-(trans-4-p-heptylphenylcyclohexoxy)-propane
1-tribromosilyl-3-(trans-4-p-methoxyphenylcyclohexoxy)-propane
1-tribromosilyl-3-(trans-4-p-ethoxyphenylcyclohexoxy)-propane
1-tribromosilyl-3-(trans-4-p-propoxyphenylcyclohexoxy)-propane
1-tribromosilyl-3-(trans-4-p-butoxyphenylcyclohexoxy)-propane
1-tribromosilyl-3-(trans-4-p-pentoxyphenylcyclohexoxy)-propane
1-tribromosilyl-3-(trans-4-p-fluorophenylcyclohexoxy)-propane
1-tribromosilyl-3-(trans-4-p-chlorophenylcyclohexoxy)-propane
1-tribromosilyl-3-(trans-4-p-bromophenylcyclohexoxy)-propane
1-tribromosilyl-3-(trans-4-p-cyanophenylcyclohexoxy)-propane
1-tribromosilyl-3-(trans-4-(trans-4-propylcyclohexyl)-cylohexoy)-propane
1-tribromosilyl-3-(trans-4-(trans-4-butylcyclohexyl)cyclohexoxy)-propane
1-tribromosilyl-3-(trans-4-(trans-4-pentylcyclohexyl)-cyclohexoxy)-propane
1-tribromosilyl-3-(trans-4-(trans-4-hexylcyclohexyl)cyclohexoxy)-propane cyclohexoxy)-propane
1-tribromosilyl-3-(trans-4-(trans-4-heptylcyclohexyl)-cyclohexoxy)-propane
1-tribromosilyl-4-(p-trans-4-propylcyclohexylphenoxy)-butane
1-tribromosilyl-5-(p-trans-4-propylcyclohexylphenoxy)-pentane
1-tribromosilyl-6-(p-trans-4-propylcyclohexylphenoxy)-hexane
1-tribromosilyl-2-methyl-3-(p-trans-4-propylcyclohexylphenoxy-propane.

EXAMPLE 3

15.5 ml of iodosilane and 0.2 ml of a 0.1 molar solution of hexachloroplatinic(IV) acid in isopropanol are added to a solution of 25.8 g of 3-(p-trans-4-propylcyclohexylphenoxy)-propene in 50 ml of methylene chloride. The mixture is stirred under reflux for two days and the solvent and excess iodosilane are then distilled off. The resulting 1-iodosilyl-3-(p-trans-4-propylcyclohexylphen oxy)-propane is used for surface treatment in a 0.1 to 1% solution in 1,1,1-trichloroethane.

The following compounds are obtained analogously:
1-iodosily-3-pcyclohexylphenoxy-propane
1-iodosily-3-(p-trans-4-methylcyclohexylphenoxy)-propane
1-iodosily-3-(p-trans-4-ethylcyclohexylphenoxy)-propane
1-iodosily-3-(p-trans-4-butylcyclohexylphenoxy)-propane
1-iodosilyl-3-(p-trans-4-isobutylcyclohexylphenoy)-propane
1-iodosilyl-3-(p-trans-4-sec. butylcyclohexylphenoxy)-propane
1-iodosilyl-3-(p-trans-4-pentylcyclohexylphenoxy)-propane
1-iodosilyl-3-(p-trans-4-hexylcyclohexylphenoxy)-propane
1-iodosilyl-3-(p-trans-4-heptylcyclohexylphenoxy)-propane
1-iodosilyl-3-(p-trans-4-octylcyclohexylphenoxy)-propane
1-iodosilyl-3-(p-trans-4-nonylcyclohexylphenoxy)-propane
1-iodosilyl-3-(p-trans-4-decylcyclohexylphenoxy)-propane
1-iodosilyl-3-pbiphenyloxy-propane
1-iodosilyl-3-(4'-methyl-biphenylyl-4-oxy)-propane
1-iodosilyl-3-(4'-ethyl-biphenylyl-4-oxy)-propane
1-iodosilyl-3-(4'-propyl-biphenylyl-4-oxy)-propane
1-iodosilyl-3-(4'-butyl-biphenylyl-4-oxy)-propane
1-iodosilyl-3-(4'-pentyl-biphenylyl-4-oxy)-propane
1-iodosilyl-3-(4'-hexyl-biphenylyl-4-oxy)-propane
1-iodosilyl-3-(4'-heptyl-biphenylyl-4-oxy)-propane
1-iodosilyl-3-(4'-octyl-biphenylyl-4-oxy)-propane
1-iodosilyl-3-(4'-nonyl-biphenylyl-4-oxy)-propane
1-iodosilyl-3-(4'-decyl-biphenylyl-4-oxy)-propane
1-iodosilyl-3-(4'-methoxy-biphenylyl-4-oxy)-propane
1-iodosilyl-3-(4'-ethoxy-biphenylyl-4-oxy)-propane
1-iodosilyl-3-(4'-propoxy-biphenylyl-4-oxy)-propane
1-iodosilyl-3-(4'-butoxy-biphenylyl-4-oxy)-propane
1-iodosilyl-3-(4'-pentoxy-biphenylyl-4-oxy)-propane
1-iodosilyl-3-(4'-hexoxy-biphenylyl-4-oxy)-propane
1-iodosilyl-3-(4'-heptoxy-biphenylyl-4-oxy)-propane
1-iodosilyl-3-(4'-methoxymethyl-biphenylyl-4-oxy)-propane
1-iodosilyl-3-(4'-methoxymethoxy-biphenylyl-4-oxy)-propane
1-iodosilyl-3-(4'-fluoro-biphenylyl-4-oxy)-propane
1-iodosilyl-3-(4'-chloro-biphenylyl-4-oxy)-propane
1-iodosilyl-3-(4'-bromo-biphenylyl-4-oxy)-propane
1-iodosilyl-3-(4'-cyano-biphenylyl-4-oxy)-propane
1-iodosilyl-3-(trans-4-phenylcyclohexoxy)-propane
1-iodosilyl-3-(trans-4-p-tolylcyclohexoxy)-propane
1-iodosilyl-3-(trans-4-p-ethylphenylcyclohexoxy)-propane
1-iodosilyl-3-(trans-4-p-propylphenylcyclohexoxy)-propane
1-iodosilyl-3-(trans-4-p-butylphenylcyclohexoxy)-propane
1-iodosilyl-3-(trans-4-p-pentylphenylcyclohexoxy)-propane
1-iodosilyl-3-(trans-4-p-hexylphenylcyclohexoxy)-propane
1-iodosilyl-3-(trans-4-p-heptylphenylcyclohexoxy)-propane
1-iodosilyl-3-(trans-4-p-methoxyphenylcyclohexoxy)-propane.
1-iodosilyl-3-(trans-4-p-ethoxyphenylcyclohexoxy)-propane
1-iodosilyl-3-(trans-4-p-propoxyphenylcyclohexoxy)-propane
1-iodosilyl-3-(trans-4-p-butoxyphenylcyclohexoxy)-propane
1-iodosilyl-3-(trans-4-p-pentoxyphenylcyclohexoxy)-propane
1-3-(trans-4-p-fluorophenylcyclohexoxy)-propane
1-iodosilyl-3-(trans-4-p-chlorophenylcyclohexoxy)-propane
1-iodosilyl-3-(trans-4-p-bromophenylcyclohexoxy)-propane
1-iodosilyl-3-(trans-4-p-cyanophenylcyclohexoxy)-propane
1-iodosilyl-3-(trans-4-(trans-4-propylcyclohexyl)-cyclohexoxy)-propane
1-iodosilyl-3-(trans-4-(trans-4-butylcyclohexyl)-cyclohexoxy)-propane
1-iodosilyl-3-(trans-4-(trans-4-pentylcyclohexyl)-cyclohexoxy)-propane 1-iodosilyl-3-(trans-4-(trans-4-hexylcyclohexyl)-cyclohexoxy)-propane
1-iodosilyl-3-(trans-4-(trans-4-heptylcyclohexyl)-cyclohexoxy)-propane
1-iodosilyl-4-(p-trans-4-propylcyclohexylphenoxy)-butane
1-iodosilyl-5-(p-trans-4-propylcyclohexylphenoxy)-pentane
1-iodosilyl-6-(p-trans-4-propylcyclohexylphenoxy)-hexane
1-iodosilyl-2-methyl-3-(p-trans-4-propylcyclohexylphenoxy)-propane.

EXAMPLE 4

48.6 g of ammonium isothiocyanate are suspended in 50 ml of tetrahydrofuran. A solution of 39.4 g of 1-trichlorosilyl-3-(p-trans-4-propylcyclohexylphenoxy)-propane (prepared analogously to Example 2 from trichlorosilane and 3-(p-trans-4-propylcyclohexylphenoxy)-propene) in 40 ml of tetrahydrofuran is added to the suspension. The mixture is stirred under reflux for 24 hours. It is filtered over a frit under nitrogen and the solvent is distilled off. 1-Triisothiocyanatosilyl-3-(p-trans-4-propylcyclohexylphenoxy)-propane thus obtained is used directly for surface treatment as a 0.1 to 1% solution.

The following compounds are obtained analogously:
1-triisothiocyanatosilyl-3-p-cyclohexylphenoxy-propane
1-triisothiocyanatosilyl-3-(p-trans-4-methylcyclohexylphenoxy)-propane
1-triisothiocyanatosilyl-3-(p-trans-4-ethylcyclohexylphenoxy)-propane
1-triisothiocyanatosilyl-3-(p-trans-4-butylcyclohexylphenoxy)-propane
1-triisothiocyanatosilyl-3-(p-trans-4-isobutylcyclohexylphenoxy)-propane
1-triisothiocyanatosilyl-3-(p-trans-4-sec.-butylcyclohexylphenoxy)-propane
1-triisothiocyanatosilyl-3-(p-trans-4-pentylcyclohexylphenoxy)-propane
1-triisothiocyanatosilyl-3-(p-trans-4-hexylcyclohexylphenoxy)-propane
1-triisothiocyanatosilyl-3-(p-trans-4-heptylcyclohexylphenoxy)-propane
1-triisothiocyanatosilyl-3-(p-trans-4-octylcyclohexylphenoxy)-propane 1-triisothiocyanatosilyl-3-(p-trans-4-nonylcyclohexyl-phenoxy)-propane
1-triisothiocyanatosilyl-3-(p-trans-4-decylcyclohexyl-phenoxy)-propane
1-triisothiocyanatosilyl-3-p-biphenyloxy-propane
1-triisothiocyanatosilyl-3-(4'-methyl-biphenylyl-4-oxy)-propane
1-triisothiocyanatosilyl-3-(4'-ethyl-biphenylyl-4-oxy)-propane
1-trisothiocyanatosilyl-3-(4'-propyl-biphenylyl-4-oxy)-propane
1-triisothiocyanatosilyl-3-(4'-butyl-biphenylyl-4-oxy)-propane
1-triisothiocyanatosilyl-3-(4'-pentyl-biphenylyl-4-oxy)-propane
1-triisothiocyanatosilyl-3-(4'-hexyl-biphenylyl-4-oxy)-propane
1-triisothiocyanatosilyl-3-(4'-heptyl-biphenylyl-4-oxy)-propane
1-triisothiocyanatosilyl-3-(4'-octyl-biphenylyl-4-oxy)-propane
1-triisothiocyanatosilyl-3-(4'-nonyl-biphenylyl-4-oxy)-propane
1-triisothiocycanatosilyl-3-(4'-decyl-biphenylyl-4-oxy)-propane
1-triisothiocyanatosilyl-3-(4'-methoxy-biphenylyl-4-oxy)-propane
1-triisothiocyanatosilyl-3-(4'-ethoxy-biphenylyl-4-oxy)-propane
1-triisothiocyanatosilyl-3-(4'-propoxy-biphenylyl-4-oxy)-propane
1-triisothiocyanatosilyl-3-(4'-butoxy-biphenylyl-4-oxy)-propane
1-triisothiocyanatosilyl-3-(4'-pentoxy-biphenylyl-4-oxy)-propane
1-triisothiocyanatosilyl-3-(4'-hexoxy-biphenylyl-4-oxy)-propane
1-triisothiocyanatosilyl-3-(4'-heptoxy-biphenylyl-4-oxy)-propane
1-triisothiocyanatosilyl-3-(4'-methoxymethyl-biphenylyl-4-oxy)-propane
1-triisothiocyanatosilyl-3-(4'-methoxymethoxy-biphenylyl-4-oxy)-propane
1-triisothiocyanatosilyl-3-(4'-fluoro-biphenylyl-4-oxy)-propane
1-triisothiocyanatosilyl-3-(4'-chloro-biphenylyl-4-oxy)-propane
1-triisothiocyanatosilyl-3-(4'-bromo-biphenylyl-4-oxy)-propane
1-triisothiocyanatosilyl-3-(4'-cyano-biphenylyl-4-oxy)-propane
1-triisothiocyanatosilyl-3-(trans-4-phenylcyclohexoxy)-propane
1-triisothiocyanatosilyl-3-(trans-4-p-tolylcyclohexoxy)-propane
1-triisothiocyanatosilyl-3-(trans-4-p-ethylphenylcyclohexoxy)-propane
1-triisothiocyanatosilyl-3-(trans-4-p-propylphenylcyclohexoxy)-propane
1-triisothiocyanatosilyl-3-(trans-4-p-butylphenylcyclohexoxy)-propane
1-triisothiocyanatosilyl-3-(trans-4-p-pentylphenylcyclohexoxy)-propane
1-triisothiocyanatosilyl-3-(trans-4-p-hexylphenylcyclohexoxy)-propane
1-triisothiocyanatosilyl-3-(trans-4-p-heptylphenylcyclohexoxy)-propane
1-triisothiocyanatosilyl-3-(trans-4-p-methoxyphenylcyclohexoxy)-propane
1-triisothiocyanatosilyl-3-(trans-4-p-ethoxyphenylcyclohexoxy)-propane
1-triisothiocyanatosilyl-3-(trans-4-p-propoxyphenylcyclohexoxy)-propane
1-triisothiocyanatosilyl-3-(trans-4-p-butoxyphenylcyclohexoxy)-propane
1-triisothiocyanatosilyl-3-(trans-4-p-pentoxyphenylcyclohexoxyl-propane
1-triisothiocyanatosilyl-3-(trans-4-p-fluorophenylcyclohexoxy)-propane
1-triisothiocyanatosilyl-3-(trans-4-p-chlorophenylcyclo-hexoxy)-propane
1-triisothiocyanatosilyl-3-(trans-4-p-bromophenylcyclo-hexoxy)-propane
1-triisothiocyanatosilyl-3-(trans-4-p-cyanophenylcyclohexoxy)-propane
1-triisothiocyanatosilyl-3-(trans-4-(trans-4-propylcyclohexyl)-cyclohexoxy)-propane
1-triisothiocyanatosilyl-3-(trans-4-(trans-4-butylcyclohexyl)-cyclohexoxy)-propane
1-triisothiocyanatosilyl-3-(trans-4-(trans-4-pentylcyclohexyl)-cyclohexoxy)-propane
1-triisothiocyanatosilyl-3-(trans-4-(trans-4-hexylcyclohexyl)-cyclohexoxy)-propane
1-triisothiocyanatosilyl-3-(trans-4-(trans-4-heptylcyclohexyl)-cyclohexoxy)-propane
1-triisothiocyanatosilyl-4-(p-trans-4-propylcyclohexyl-phenoxy)-butane
1-triisothiocyanatosilyl-5-(p-trans-4-propylcyclohexyl-phenoxy)-pentane
1-triisothiocyanatosilyl-6-(p-trans-4-propylcyclohexyl-phenoxy)-hexane
1-triisothiocyanatosilyl-2-methyl-3-(p-trans-4-propyl-cyclohexylphenoxy)-propane.

EXAMPLE 5

99 g of trichlorosilane and 1 ml of a 0.1 molar solution of hexachloroplatinic(IV) acid in isopropanol are added to a solution of 100 g of 3-(4-phenylphenoxy)-propene (m. 84°–85°; obtainable by reaction of 4-phenyl-phenol with allyl bromide) in 230 ml of methylene chloride. After boiling under reflux overnight, the solvent and excess trichlorosilane are distilled off. 1-Trichlorosilyl-3-(4-phenylphenoxy)-propane (m. 24°–26°) remains, and is used for surface treatment as a 0.1 to 1% solution.

The following compounds are obtained analogously:
1-trichlorosilyl-3-p-cyclohexylphenoxy-propane
1-trichlorosilyl-3-(p-trans-4-methylcyclohexylphenoxy)-propane
1-trichlorosilyl-3-(p-trans-4-ethylcyclohexylphenoxy)-propane
1-trichlorosilyl-3-(p-trans-4-butylcyclohexylphenoxy)-propane
1-trichlorosilyl-3-(p-trans-4-isobutylcyclohexylphenoxy)-propane
1-trichlorosilyl-3-(p-trans-4-sec.-butylcyclohexyl-phenoxy)-propane
1-trichlorosilyl-3-(p-trans-4-pentylcyclohexylphenoxy)-propane
1-trichlorosilyl-3-(p-trans-4-hexylcyclohexylphenoxy)-propane
1-trichlorosilyl-3-(p-trans-4-heptylcyclohexylphenoxy)-propane
1-trichlorosilyl-3-(p-trans-4-octylcyclohexylphenoxy)-propane 1-trichlorosilyl-3-(p-trans-4-nonylcyclohexylphenoxy)-propane
1-trichlorosilyl-3-(p-trans-4-decylcyclohexylphenoxy)-propane
1-trichlorosilyl-3-p-biphenyloxy-propane
1-trichlorosilyl-3-(4'-methyl-biphenylyl-4-oxy)-propane
1-trichlorosilyl-3-(4'-ethyl-biphenylyl-4-oxy)-propane
1-trichlorosilyl-3-(4'-propyl-biphenylyl-4-oxy)-propane
1-trichlorosilyl-3-(4'-butyl-biphenylyl-4-oxy)-propane
1-trichlorosilyl-3-(4'-pentyl-biphenylyl-4-oxy)-propane
1-trichlorosilyl-3-(4'-hexyl-biphenylyl-4-oxy)-propane
1-trichlorosilyl-3-(4'-heptyl-biphenylyl-4-oxy)-propane
1-trichlorosilyl-3-(4'-octyl-biphenylyl-4-oxy)-propane
1-trichlorosilyl-3-(4'-nonyl-biphenylyl-4-oxy)-propane
1-trichlorosilyl-3-(4'-decyl-biphenylyl-4-oxy)-propane
1-trichlorosilyl-3-(4'-methoxy-biphenylyl-4-oxy)-propane
1-trichlorosilyl-3-(4'-ethoxy-biphenylyl-4-oxy)-propane
1-trichlorosilyl-3-(4'-propoxy-biphenylyl-4-oxy)-propane
1-trichlorosilyl-3-(4'-butoxy-biphenylyl-4-oxy)-propane
1-trichlorosilyl-3-(4'-pentoxy-biphenylyl-4-oxy)-propane
1-trichlorosilyl-3-(4'-hexoxy-biphenylyl-4-oxy)-propane
1-trichlorosilyl-3-(4'-heptoxy-biphenylyl-4-oxy)-propane
1-trichlorosilyl-3-(4'-methoxymethyl-biphenylyl-4-oxy)-propane
1-trichlorosilyl-3-(4'-methoxymethoxy-biphenylyl-4-oxy)-propane
1-trichlorosilyl-3-(4'-fluoro-biphenylyl-4-oxy)-propane
1-trichlorosilyl-3-(4'-chloro-biphenylyl-4-oxy)-propane
1-trichlorosilyl-3-(4'-bromo-biphenylyl-4-oxy)-propane
1-trichlorosilyl-3-(4'-cyano-biphenylyl-4-oxy)-propane
1-trichlorosilyl-3-(trans-4-phenylcyclohexoxy)-propane
1-trichlorosilyl-3-(trans-4-p-tolylcyclohexoxy)-propane
1-trichlorosilyl-3-(trans-4-p-ethylphenylcyclohexoxy)-propane
1-trichlorosilyl-3-(trans-4-p-propylphenylcyclohexoxy)-propane
1-trichlorosilyl-3-(trans-4-p-butylphenylcyclohexoxy)-propane
1-trichlorosilyl-3-(trans-4-p-pentylphenylcyclohexoxy)-propane
1-trichlorosilyl-3-(trans-4-p-hexylphenylcyclohexoxy)-propane
1-trichlorosilyl-3-(trans-4-p-heptylphenylcyclohexoxy)-propane
1-trichlorosilyl-3-(trans-4-p-methoxyphenylcyclohexoxy)-propane
1-trichlorosilyl-3-(trans-4-p-ethoxyphenylcyclohexoxy)-propane
1-trichlorosilyl-3-(trans-4-p-propoxyphenylcyclohexoxy)-propane
1-trichlorosilyl-3-(trans-4-p-butoxyphenylcyclohexoxy)-propane
1-trichlorosilyl-3-(trans-4-p-pentoxyphenylcyclohexoxy)-propane
1-trichlorosilyl-3-(trans-4-p-fluorophenylcyclohexoxy)-propane
1-trichlorosilyl-3-(trans-4-p-chlorophenylcyclohexoxy)-propane
1-trichlorosilyl-3-(trans-4-p-bromophenylcyclohexoxy)-propane
1-trichlorosilyl-3-(trans-4-p-cyanophenylcyclohexoxy)-propane
1-trichlorosilyl-3-(trans-4-(trans-4-propylcyclohexyl)-cyclohexoxy)-propane
1-trichlorosilyl-3-(trans-4-(trans-4-butylcyclohexyl)-cyclohexoxy)-propane
1-trichlorosilyl-3-(trans-4-(trans-4-pentylcyclohexyl)-cyclohexoxy)-propane
1-trichlorosilyl-3-(trans-4-(trans-4-hexylcyclohexyl)-cyclohexoxy)-propane
1-trichlorosilyl-3-(trans-4-(trans-4-heptylcyclohexyl)-cyclohexoxy)-propane
1-trichlorosilyl-4-(p-trans-4-propylcyclohexylphenoxy)-butane
1-trichlorosilyl-5-(p-trans-4-propylcyclohexylphenoxy)-pentane
1-trichlorosilyl-6-(p-trans-4-propylcyclohexylphenoxy)-hexane
1-trichlorosilyl-2-methyl-3-(p-trans-4-propylcyclohexylphenoxy)-propane.

EXAMPLE 6

9.6 g of triethoxysilane and 0.4 ml of a 0.01 molar solution of $H_2PtCl_6$ in isopropanol are added to a solution of 10 g of 3-(p-trans-4-propylcyclohexylphenoxy)-propene in 10 ml of methylene chloride. The mixture is stirred at 35° C. for 2 days and the solvent and excess triethoxysilane are then distilled off. Crude 1-triethoxysilyl-3-(p-trans-4-propyl-cyclohexylphenoxy)-propane thus obtained is used for surface treatment in a 0.1% solution in ethanol.

200 MHz $^1$H-NMR (CDCl$_3$): 0.60–2.40 (30H, aliphatic H), 3.72 (q, 6H, Si[OCH$_2$CH$_3$]$_3$), 3.77 (t, 2H, OCH$_2$CH$_2$), 6.64–7.07 (AA'BB', 4H, aromatic H).

The following compounds are obtained analogously:
1-triethoxysilyl-3-p-cyclohexylphenoxy-propane
1-triethoxysilyl-3-(p-trans-4-methylcyclohexylphenoxy)-propane
1-triethoxysilyl-3-(p-trans-4-ethylcyclohexylphenoxy)-propane
1-triethoxysilyl-3-(p-trans-4-butylcyclohexylphenoxy)-propane
1-triethoxysilyl-3-(p-trans-4-isobutylcyclohexylphenoxy)-propane
1-triethoxysilyl-3-(p-trans-4-sec.-butylcyclohexylphenoxy)-propane
1-triethoxysilyl-3-(p-trans-4-pentylcyclohexylphenoxy)-propane
1-triethoxysilyl-3-(p-trans-4-hexylcyclohexylphenoxy)-propane
1-triethoxysilyl-3-(p-trans-4-heptylcyclohexylphenoxy)-propane
1-triethoxysilyl-3-(p-trans-4-octylcyclohexylphenoxy)-propane
1-triethoxysilyl-3-(p-trans-4-nonylcyclohexylphenoxy)-propane
1-triethoxysilyl-3-(p-trans-4-decylcyclohexylphenoxy)-propane
1-triethoxysilyl-3-p-biphenyloxy-propane
1-triethoxysilyl-3-(4'-methyl-biphenylyl-4-oxy)-propane
1-triethoxysilyl-3-(4'-ethyl-biphenylyl-4-oxy)-propane
1-triethoxysilyl-3-(4'-propyl-biphenylyl-4-oxy)-propane
1-triethoxysilyl-3-(4'-butyl-biphenylyl-4-oxy)-propane
1-triethoxysilyl-3-(4'-pentyl-biphenylyl-4-oxy)-propane
1-triethoxysilyl-3-(4'-hexyl-biphenylyl-4-oxy)-propane
1-triethoxysilyl-3-(4'-heptyl-biphenylyl-4-oxy)-propane
1-triethoxysilyl-3-(4'-octyl-biphenylyl-4-oxy)-propane
1-triethoxysilyl-3-(4'-nonyl-biphenylyl-4-oxy)-propane
1-triethoxysilyl-3-(4'-decyl-biphenylyl-4-oxy)-propane 1-triethoxysilyl-3-(4'-methoxy-biphenylyl-4-oxy)-propane
1-triethoxysilyl-3-(4'-ethoxy-biphenylyl-4-oxy)-propane
1-triethoxysilyl-3-(4'-propoxy-biphenylyl-4-oxy)-propane
1-triethoxysilyl-3-(4'-butoxy-biphenylyl-4-oxy)-propane
1-triethoxysilyl-3-(4'-pentoxy-biphenylyl-4-oxy)-propane
1-triethoxysilyl-3-(4'-hexoxy-biphenylyl-4-oxy)-propane
1-triethoxysilyl-3-(4'-heptoxy-biphenylyl-4-oxy)-propane
1-triethoxysilyl-3-(4'-methoxymethyl-biphenylyl-4-oxy)-propane
1-triethoxysilyl-3-(4'-methoxymethoxy-biphenylyl-4-oxy)-propane
1-triethoxysilyl-3-(4'-fluoro-biphenylyl-4-oxy)-propane
1-triethoxysilyl-3-(4'-chloro-biphenylyl-4-oxy)-propane
1-triethoxysilyl-3-(4'-bromo-biphenylyl-4-oxy)-propane
1-triethoxysilyl-3-(4'-cyano-biphenylyl-4-oxy)-propane
1-triethoxysilyl-3-(trans-4-phenylcyclohexoxy)-propane
1-triethoxysilyl-3-(trans-4-p-tolylcyclohexoxy)-propane
1-triethoxysilyl-3-(trans-4-p-ethylphenylcyclohexoxy)-propane
1-triethoxysilyl-3-(trans-4-p-propylphenylcyclohexoxy)-propane
1-triethoxysilyl-3-(trans-4-p-butylphenylcyclohexoxy)-propane
1-triethoxysilyl-3-(trans-4-p-pentylphenylcyclohexoxy)-propane
1-triethoxysilyl-3-(trans-4-p-hexylphenylcyclohexoxy)-propane
1-triethoxysilyl-3-(trans-4-p-heptylphenylcyclohexoxy)-propane
1-triethoxysilyl-3-(trans-4-p-methoxyphenylcyclohexoxy)-propane
1-triethoxysilyl-3-(trans-4-p-ethoxyphenylcyclohexoxy)-propane
1-triethoxysilyl-3-(trans-4-p-propoxyphenylcyclohexoxy)-propane
1-triethoxysilyl-3-(trans-4-p-butoxyphenylcyclohexoxy)-propane
1-triethoxysilyl-3-(trans-4-p-pentoxyphenylcyclohexoxy)-propane
1-triethoxysilyl-3-(trans-4-p-fluorophenylcyclohexoxy)-propane
1-triethoxysilyl-3-(trans-4-p-chlorophenylcyclohexoxy)-propane
1-triethoxysilyl-3-(trans-4-p-bromophenylcyclohexoxy)-propane
1-triethoxysilyl-3-(trans-4-p-cyanophenylcyclohexoxy)-propane
1-triethoxysilyl-3-(trans-4-(trans-4-propylcyclohexyl)-cyclohexoxy)-propane
1-triethoxysilyl-3-(trans-4-(trans-4-butylcyclohexyl)-cyclohexoxy)-propane
1-triethoxysilyl-3-(trans-4-(trans-4-pentylcyclohexyl)-cyclohexoxy)-propane
1-triethoxysilyl-3-(trans-4-(trans-4-hexylcyclohexyl)-cyclohexoxy)-propane
1-triethoxysilyl-3-(trans-4-(trans-4-heptylcyclohexyl)-cyclohexoxy)-propane
1-triethoxysilyl-4-(p-trans-4-propylcyclohexylphenoxy)-butane
1-triethoxysilyl-5-(p-trans-4-propylcyclohexylphenoxy)-pentane
1-triethoxysilyl-6-(p-trans-4-propylcyclohexylphenoxy)-hexane
1-triethoxysilyl-2-methyl-3-(p-trans-4-propylcyclohexyl-phenoxy)-propane.

EXAMPLE 7

0.1 mole of 1-chloro-3-(p-trans-4-propylcyclohexylphenoxy)-propane (prepared from 1-bromo-3-chloropropane and p-trans-4-propylcyclohexylphenol) is dissolved in 250 ml of methylene chloride and, after addition of 10 ml of triethylamine and 0.2 mole of trimethoxysilane, the mixture is heated at the reflux temperature for 24 hours. It is allowed to cool and freed by filtration from the triethylammonium chloride which has separated out. After the excess solvent has been distilled off under reduced pressure, 1-trimethoxysilyl-3-(p-trans-4-propylcyclohexylphenoxy)-propane is obtained, and is used for surface treatment in a 0.1 to 1% solution in methanol.

The following compounds are obtained analogously:
1-trimethoxysilyl-3-p-cyclohexylphenoxy-propane
1-trimethoxysilyl-3-(p-trans-4-methylcyclohexylphenoxy)-propane
1-trimethoxysilyl-3-(p-trans-4-ethylcyclohexylphenoxy)-propane
1-trimethoxysilyl-3-(p-trans-4-butylcyclohexylphenoxy)-propane
1-trimethoxysilyl-3-(p-trans-4-isobutylcyclohexylphenoxy)-propane
1-trimethoxysilyl-3-(p-trans-4-sec.-butylcyclohexylphenoxy)-propane
1-trimethoxysilyl-3-(p-trans-4-pentylcyclohexylphenoxy)-propane
1-trimethoxysilyl-3-(p-trans-4-hexylcyclohexylphenoxy)-propane
1-trimethoxysilyl-3-(p-trans-4-heptylcyclohexylphenoxy)-propane
1-trimethoxysilyl-3-(p-trans-4-octylcyclohexylphenoxy)-propane
1-trimethoxysilyl-3-(p-trans-4-nonylcyclohexylphenoxy)-propane
1-trimethoxysilyl-3-(p-trans-4-decylcyclohexylphenoxy)-propane
1-trimethoxysilyl-3-p-biphenyloxy-propane
1-trimethoxysilyl-3-(4'-methyl-biphenylyl-4-oxy)-propane
1-trimethoxysilyl-3-(4'-ethyl-biphenylyl-4-oxy)-propane
1-trimethoxysilyl-3-(4'-propyl-biphenylyl-4-oxy)-propane
1-trimethoxysilyl-3-(4'-butyl-biphenylyl-4-oxy)-propane
1-trimethoxysilyl-3-(4'-pentyl-biphenylyl-4-oxy)-propane
1-trimethoxysilyl-3-(4'-hexyl-biphenylyl-4-oxy)-propane
1-trimethoxysilyl-3-(4'-heptyl-biphenylyl-4-oxy)-propane
1-trimethoxysilyl-3-(4'-octyl-biphenylyl-4-oxy)-propane
1-trimethoxysilyl-3-(4'-nonyl-biphenylyl-4-oxy)-propane
1-trimethoxysilyl-3-(4'-decyl-biphenylyl-4-oxy)-propane
1-trimethoxysilyl-3-(4'-methoxy-biphenylyl-4-oxy)-propane
1-trimethoxysilyl-3-(4'-ethoxy-biphenylyl-4-oxy)-propane
1-trimethoxysilyl-3-(4'-propoxy-biphenylyl-4-oxy)-propane 1-trimethoxysilyl-3-(4'-butoxy-biphenylyl-4-oxy)-propane
1-trimethoxysilyl-3-(4'-pentoxy-biphenylyl-4-oxy)-propane
1-trimethoxysilyl-3-(4'-hexoxy-biphenylyl-4-oxy)-propane
1-trimethoxysilyl-3-(4'-heptoxy-biphenylyl-4-oxy)-propane
1-trimethoxysilyl-3-(4'-methoxymethyl-biphenylyl-4-oxy)-propane
1-trimethoxysilyl-3-(4'-methoxymethoxy-biphenylyl-4-oxy)-propane
1-trimethoxysilyl-3-(4'-fluoro-biphenylyl-4-oxy)-propane
1-trimethoxysilyl-3-(4'-chloro-biphenylyl-4-oxy)-propane
1-trimethoxysilyl-3-(4'-bromo-biphenylyl-4-oxy)-propane
1-trimethoxysilyl-3-(4'-cyano-biphenylyl-4-oxy)-propane
1-trimethoxysilyl-3-(trans-4-phenylcyclohexoxy)-propane
1-trimethoxysilyl-3-(trans-4-p-tolylcyclohexoxy)-propane
1-trimethoxysilyl-3-(trans-4-p-ethylphenylcyclohexoxy)-propane
1-trimethoxysilyl-3-(trans-4-p-propylphenylcyclohexoxy)-propane
1-trimethoxysilyl-3-(trans-4-p-butylphenylcyclohexoxy)-propane
1-trimethoxysilyl-3-(trans-4-p-pentylphenylcyclohexoxy)-propane
1-trimethoxysilyl-3-(trans-4-p-hexylphenylcyclohexoxy)-propane
1-trimethoxysilyl-3-(trans-4-p-heptylphenylcyclohexoxy)-propane
1-trimethoxysilyl-3-(trans-4-p-methoxyphenylcyclohexoxy)-propane
1-trimethoxysilyl-3-(trans-4-p-ethoxyphenylcyclohexoxy)-propane
1-trimethoxysilyl-3-(trans-4-p-propoxyphenylcyclohexoxy)-propane
1-trimethoxysilyl-3-(trans-4-p-butoxyphenylcyclohexoxy)-propane
1-trimethoxysilyl-3-(trans-4-p-pentoxyphenylcyclohexoxy)-propane
1-trimethoxysilyl-3-(trans-4-p-fluorophenylcyclohexoxy)-propane
1-trimethoxysilyl-3-(trans-4-p-chlorophenylcyclohexoxy)-propane
1-trimethoxysilyl-3-(trans-4-p-bromophenylcyclohexoxy)-propane
1-trimethoxysilyl-3-(trans-4-p-cyanophenylcyclohexoxy)-propane
1-trimethoxysilyl-3-(trans-4-(trans-4-propylcyclohexyl)-cyclohexoxy)-propane
1-trimethoxysilyl-3-(trans-4-(trans-4-butylcyclohexyl)-cyclohexoxy)-propane
1-trimethoxysilyl-3-(trans-4-(trans-4-pentylcyclohexyl)-cyclohexoxy)-propane
1-trimethoxysilyl-3-(trans-4-(trans-4-hexylcyclohexyl)-cyclohexoxy)-propane
1-trimethoxysilyl-3-(trans-4-(trans-4-heptylcyclohexyl)-cyclohexoxy)-propane
1-trimethoxysilyl-4-(p-trans-4-propylcyclohexylphenoxy)-butane
1-trimethoxysilyl-5-(p-trans-4-propylcyclohexylphenoxy)-pentane
1-trimethoxysilyl-6-(p-trans-4-propylcyclohexylphenoy)-hexane
1-trimethoxysilyl-2-methyl-3-(p-trans-4-propylcyclohexylphenoxy)-propane.

EXAMPLE 8

0.1 mole of 1-dichlorosilyl-3-(p-trans-4-propylcyclohexylphenoxy)-propane (obtained analogously to the preparation described for the corresponding trichloromethyl compound) is slowly added dropwise to a suspension of 0.25 mole equivalent of a strongly basic anion exchanger in 200 ml of isopropanol at room temperature. Stirring is then continued overnight. The exchanger is removed by filtration and a solution of 1-disopropyloxysilyl 3-(p-trans-4-propyl-cyclohexylphenoxy)-propane, which is suitable for use in surface treatment by means of printing processes, is thus obtained.

The following compounds are obtained analogously:
1-diisopropyloxysilyl-3-p-cyclohexylphenoxy-propane
1-diisopropyloxysilyl-3-(p-trans-4-methylcyclohexylphenoxy)-propane
1-diisopropyloxysilyl-3-(p-trans-4-ethylcyclohexylphenoxy)-propane
1-diisopropyloxysilyl-3-(p-trans-4-butylcyclohexylphenoxy)-propane
1-diisopropyloxysilyl-3-(p-trans-4-isobutylcyclohexylphenoxy)-propane
1-diisopropyloxysilyl-3-(p-trans-4-sec.-butylcyclohexyl-phenoxy)-propane
1-diisopropyloxysilyl-3-(p-trans-4-pentylcyclohexylphenoxy)-propane
1-diisopropyloxysilyl-3-(p-trans-4-hexylcyclohexylphenoxy)-propane
1-diisopropyloxysilyl-3-(p-trans-4-heptylcyclohexylphenoxy)-propane
1-diisopropyloxysilyl-3-(p-trans-4-octylcyclohexylphenoxy)-propane
1-diisopropyloxysilyl-3-(p-trans-4-nonylcyclohexylphenoxy)-propane
1-diisopropyloxysilyl-3-(p-trans-4-decylcyclohexylphenoxy)-propane
1-diisopropyloxysilyl-3-p-biphenyloxy-propane
1-diisopropyloxysilyl-3-(4'-methylbiphenylyl-4-oxy)-propane
1-diisopropyloxysilyl-3-(4'-ethyl-biphenylyl-4-oxy)-propane
1-diisopropyloxysilyl-3-(4'-propyl-biphenylyl-4-oxy)-propane
1-diisopropyloxysilyl-3-(4'-butyl-biphenylyl-4-oxy)-propane
1-diisopropyloxysilyl-3-(4'-pentyl-biphenylyl-4-oxy)-propane
1-diisopropyloxysilyl-3-(4'-hexyl-biphenylyl-4-oxy)-propane
1-diisopropyloxysilyl-3-(4'-heptyl-biphenylyl-4-oxy)-propane
1-diisopropyloxysilyl-3-(4'-octyl-biphenylyl-4-oxy)-propane
1-diisopropyloxysilyl-3-(4'-nonyl-biphenylyl-4-oxy)-propane
1-diisopropyloxysilyl-3-(4'-decyl-biphenylyl-4-oxy)-propane
1-diisopropyloxysilyl-3-(4'-methoxy-biphenylyl-4-oxy)-propane
1-diisopropyloxysilyl-3-(4'-ethoxy-biphenylyl-4-oxy)-propane 1-diisopropyloxysilyl-3-(4'-propoxy-biphenylyl-4-oxy)-propane
1-diisopropyloxysilyl-3-(4'-butoxy-biphenylyl-4-oxy)-propane
1-diisopropyloxysilyl-3-(4'-pentoxy-biphenylyl-4-oxy)-propane
1-diisopropyloxysilyl-3-(4'-hexoxy-biphenylyl-4-oxy)-propane
1-diisopropyloxysilyl-3-(4'-heptoxy-biphenylyl-4-oxy)-propane
1-diisopropyloxysilyl-3-(4'-methoxymethyl-biphenylyl-4-oxy)-propane
1-diisopropyloxysilyl-3-(4'-methoxymethoxy-biphenylyl-4-oxy)-propane
1-diisopropyloxysilyl-3-(4'-fluoro-biphenylyl-4-oxy)-propane
1-diisopropyloxysilyl-3-(4'-chloro-biphenylyl-4-oxy)-propane
1-diisopropyloxysilyl-3-(4'-bromo-biphenylyl-4-oxy)-propane
1-diisopropyloxysilyl-3-(4'-cyano-biphenylyl-4-oxy)-propane
1-diisopropyloxysilyl-3-(trans-4-phenylcyclohexoxy)-propane
1-diisopropyloxysilyl-3-(trans-4-p-tolylcyclohexoxy)-propane
1-diisopropyloxysilyl-3-(trans-4-p-ethylphenylcyclohexoxy)-propane
1-diisopropyloxysilyl-3-(trans-4-p-propylphenylcyclohexoxy)-propane
1-diisopropyloxysilyl-3-(trans-4-p-butylphenylcyclohexoxy)-propane
1-diisopropyloxysilyl-3-(trans-4-p-pentylphenylcyclohexoxy)-propane
1-diisopropyloxysilyl-3-(trans-4-p-hexylphenylcyclohexoxy)-propane
1-diisopropyloxysilyl-3-(trans-4-p-heptylphenylcyclohexoxy)-propane
1-diisopropyloxysilyl-3-(trans-4-p-methoxyphenylcyclohexoxy)-propane
1-diisopropyloxysilyl-3-(trans-4-p-ethoxyphenylcyclohexoxy)-propane
1-diisopropyloxysilyl-3-(trans-4-p-propoxyphenylcyclohexoxy)-propane
1-diisopropyloxysilyl-3-(trans-4-p-butoxyphenylcyclohexoxy)-propane
1-diisopropyloxysilyl-3-(trans-4-p-pentoxyphenylcyclohexoxy)-propane
1-diisopropyloxysilyl-3-(trans-4-p-fluorophenylcyclohexoxy)-propane
1-diisopropyloxysilyl-3-(trans-4-p-chlorophenylcyclohexoxy)-propane
1-diisopropyloxysilyl-3-(trans-4-p-bromophenylcyclohexoxy)-propane
1-diisopropyloxysilyl-3-(trans-4-p-cyanophenylcyclohexoxy)-propane
1-diisopropyloxysilyl-3-(trans-4-(trans-4-propylcyclohexyl)-cyclohexoxy)-propane
1-diisopropyloxysilyl-3-(trans-4-(trans-4-butylcyclohexyl)-cyclohexoxy)-propane
1-diisopropyloxysilyl-3-(trans-4-(trans-4-pentylcyclohexyl)-cyclohexoxy)-propane
1-diisopropyloxysilyl-3-(trans-4-(trans-4-hexylcyclohexyl)-cyclohexoxy)-propane
1-diisopropyloxysilyl-3-(trans-4-(trans-4-heptylcyclohexyl)-cyclohexoxy)-propane
1-diisopropyloxysilyl-4-(p-trans-4-propylcyclohexylphenoxy)-butane
1-diisopropyloxysilyl-5-(p-trans-4-propylcyclohexylphenoxy)-pentane
1-diisopropyloxysilyl-6-(p-trans-4-propylcyclohexylphenoxy)-hexane
1-diisopropyloxysilyl-2-methyl-3-(p-trans-4-propylcyclohexylphenoxy)-propane.

EXAMPLE 9

10.3 ml of pyridine and 13.2 ml of acetylacetone are added to a solution of 10 g of 1-trichlorosilyl-3-(p-trans-4-propylcyclohexylphenoxy)-propane in 100 ml of methylene chloride. The mixture is stirred at room temperature for 5 hours and then filtered off from the pyridinium hydrochloride, under nitrogen. The clear solution thus obtained is concentrated. The crude 1-(tri(1-methyl-3-oxo-but-1-enyloxy)-silyl)-3-(p-trans-4-propylcyclohexylphenoxy)-propane is used for surface treatment as a 0.1% solution.

The following compounds are obtained analogously:
1-(tri(1-methyl-3-oxo-but-1-enyloxy)-silyl)-3-p-cyclohexylphenoxy-propane
1-(tri(1-methyl-3-oxo-but-1-enyloxy)-silyl)-3-(p-trans-4-methylcyclohexylphenoxy)-propane
1-(tri(1-methyl-3-oxo-but-1-enyloxy)-silyl)-3-(p-trans-4-ethylcyclohexylphenoxy)-propane
1-(tri(1-methyl-3-oxo-but-1-enyloxy)-silyl)-3-(p-trans-4-butylcyclohexylphenoxy)-propane
1-(tri(1-methyl-3-oxo-but-1-enyloxy)-silyl)-3-(p-trans-4-isobutylcyclohexylphenoxy)-propane
1-(tri(1-methyl-3-oxo-but-1-enyloxy)-silyl)-3-(p-trans-4-sec.-butylcyclohexylphenoxy)-propane
1-(tri(1-methyl-3-oxo-but-1-enyloxy)-silyl)-3-(p-trans-4-pentylcyclohexylphenoxy)-propane
1-(tri(1-methyl-3-oxo-but-1-enyloxy)-silyl)-3-(p-trans-4-hexylcyclohexylphenoxy)-propane
1-(tri(1-methyl-3-oxo-but-1-enyloxy)-silyl)-3-(p-trans-4-heptylcyclohexylphenoxy)-propane
1-(tri(1-methyl-3-oxo-but-1-enyloxy)-silyl)-3-(p-trans-4-octylcyclohexylphenoxy)-propane
1-(tri(1-methyl-3-oxo-but-1-enyloxy)-silyl)-3-(p-trans-4-nonylcyclohexylphenoxy)-propane
1-(tri-(1-methyl-3-oxo-but-1-enyloxy)-silyl)-3-(p-trans-4-decylcyclohexylphenoxy)-propane
1-(tri-(1-methyl-3-oxo-but-1-enyloxy)-silyl)-3-p-biphenyloxy-propane
1-(tri-(1-methyl-3-oxo-but-1-enyloxy)-silyl)-3-(4'-methyl-biphenylyl-4-oxy)-propane
1-(tri-(1-methyl-3-oxo-but-1-enyloxy)-silyl)-3-(4'-ethly-biphenylyl-4-oxy)-propane
1-(tri-(1-methyl-3-oxo-but-1-enyloxy)-silyl)-3-(4'-propylbiphenylyl-4-oxy)-propane
1-(tri-(1-methyl-3-oxo-but-1-enyloxy)-silyl)-3-(4'-butylbiphenylyl-4-oxy)-propane
1-(tri-(1-methyl-3-oxo-but-1-enyloxy)-silyl)-3-(4'-pentylbiphenylyl-4-oxy)-propane
1-(tri-(1-methyl-3-oxo-but-1-enyloxy)-silyl)-3-(4'-hexylbiphenylyl-4-oxy)-propane
1-(tri-(1-methyl-3-oxo-but-1-enyloxy)-silyl)-3-(4'-heptylbiphenylyl-4-oxy)-propane
1-(tri-(1-methyl-3-oxo-but-1-enyloxy)-silyl)-3-(4'-octylbiphenylyl-4-oxy)-propane
1-(tri-(1-methyl-3-oxo-but-1-enyloxy)-silyl)-3-(4'-nonylbiphenylyl-4-oxy)-propane
1-(tri-(1-methyl-3-oxo-but-1-enyloxy)-silyl)-3-(4'-decylbiphenylyl-4-oxy)-propane
1-(tri-(1-methyl-3-oxo-but-1-enyloxy)-silyl)-3-(4'-methoxy-4-oxy)-propane 1-(tri-(1-methyl-3-oxo-but-1-enyloxy)-silyl)-3-(4'-ethoxy-4-oxy)-propane
1-(tri-(1-methyl-3-oxo-but-1-enyloxy)-silyl)-3-(4'-propoxy-4-oxy)-propane
1-(tri-(1-methyl-3-oxo-but-1-enyloxy)-silyl)-3-(4'-butoxy-4-oxy)-propane
1-(tri-(1-methyl-3-oxo-but-1-enyloxy)-silyl)-3-(4'-pentoxy-4-oxy)-propane
1-(tri-(1-methyl-3-oxo-but-1-enyloxy)-silyl)-3-(4'-hexoxy-4-oxy)-propane
1-(tri-(1-methyl-3-oxo-but-1-enyloxy)-silyl)-3-(4'-heptoxy-biphenylyl4-oxy)-propane
1-(tri-(1-methyl-3-oxo-but-1-enyloxy)-silyl)-3-4'-methoxymethoxybiphenylyl-4-oxy)-propane
1-(tri-(1-methyl-3-oxo-but-1-enyloxy)-silyl)-3-(4'-methoxymethoxybiphenylyl-4-oxy)-propane 1-(tri-(1-methyl-3-oxo-but-1-enyloxy)-silyl)-3-(4'-fluorobiphenylyl-4-oxy)-propane
1-(tri-(1-methyl-3-oxo-but-1-enyloxy)-silyl)-3-(4'-chlorobiphenylyl-4-oxy)-propane
1-(tri-(1-methyl-3-oxo-but-1-enyloxy)-silyl)-3-(4'-bromobiphenylyl-4-oxy)-propane
1-(tri-(1-methyl-3-oxo-but-1-enyloxy)-silyl)-3-(4'-cyanobiphenylyl-4-oxy)-propane
1-(tri-(1-methyl-3-oxo-but-1-enyloxy)-silyl)-3-(trans-4-phenylcyclohexoxy)-propane
1-(tri-(1-methyl-3-oxo-but-1-enyloxy)-silyl)-3-(trans-4-p-tolylcyclohexoxy)-propane
1-(tri-(1-methyl-3-oxo-but-1-enyloxy)-silyl)-3-(trans-4-p-ethylphenylcyclohexoxy)-propane
1-(tri-(1-methyl-3-oxo-but-1-enyloxy)-silyl)-3-(trans-4-p-propylphenylcyclohexoxy)-propane
1-(tri-(1-methyl-3-oxo-but-1-enyloxy)-sily)-3-(trans-4-p-butyl-phenylcyclohexoxy)-propane
1-(tri-(1-methyl-3-oxo-but-1-enyloxy)-silyl)-3-(trans-4-p-pentylphenylcyclohexoxy)-propane
1-(tri-(1-methyl-3-oxo-but-1-enyloxy)-silyl)-b 3-(trans-4-p-hexylphenylcyclohexoxy)-propane phenylcyclohexoxy)-propane
1-(tri-(1-methyl-3-oxo-but-1-enyloxy)-silyl)-3-(trans-4-p-heptylphenylcyclohexoxy)-propane
1-(tri-(1-methyl-3-oxo-but-1-enyloxy)-silyl)-3-(trans-4-p-methoxyphenylcyclohexoxy)-propane
1-(tri-(1-methyl-3-oxo-but-1-enyloxy)-silyl)-3-(trans-4-p-ethoxy-phenylcyclohexoxy)-propane
1-(tri-(1-methyl-3-oxo-but-1-enyloxy)-silyl)-3-(trans-4-p-propoxyphenylcyclohexoxy)-propane
1-(tri-(1-methyl-3-oxo-but-1-enyloxy)-silyl)-3-(trans-4-p-butoxyphenylcyclohexoxy)-propane
1-(tri-(1-methyl-3-oxo-but-1-enyloxy)-silyl)-3-(trans-4-p-pentoxyphenylcyclohexoxy-propane
1-(tri-(1-methyl-3-oxo-but-1-enyloxy)-silyl)-3-(trans-4-p-fluorophenylcyclohexoxy)-propane
1-(tri-(1-methyl-3-oxo-but-1-enyloxy)-silyl)-3-(trans-4-p-chlorophenylcyclohexoxy)-propane
1-(tri-(1-methyl-3-oxo-but-1-enyloxy)-silyl)-3-(trans-4-p-bromophenylcyclohexoxy)-propane
1-(tri-(1-methyl-3-oxo-but-1-enyloxy)-silyl)-3-(trans-4-p-cyanophenylcyclohexoxy)-propane
1-(tri-(1-methyl-3-oxo-but-1-enyloxy)-silyl)-3-(trans-4-propylcyclohexyl)-cyclohexoxy)-propane
1-(tri-(1-methyl-3-oxo-but-1-enyloxy)-silyl)-3-(trans-4-butylcyclohexyl)-cyclohexoxy)-propane
1-(tri-(1-methyl-3-oxo-but-1-enyloxy)-silyl)-3-(trans-4-pentylcyclohexyl)-cyclohexoxy)-propane
1-(tri-(1-methyl-3-oxo-but-1-enyloxy)-silyl)-3-(trans-4-hexylcyclohexyl)-cyclohexoxy)-propane
1-(tri-(1-methyl-3-oxo-but-1-enyloxy)-silyl)-3-(trans-4-heptylcyclohexyl)-cyclohexoxy)-propane
1-(tri-(1-methyl-3-oxo-but-1-enyloxy)-silyl)-3-(p-trans-4-propylcyclohexylphenoxy)-butane
1-(tri-(1methyl-3-oxo-but-1-enyloxy)-silyl-3-(p-trans-4-propylcyclohexylphenoxy)-pentane
1-(tri-(1-methyl-3-oxo-but-1-enyloxy)-silyl)-b 6-(p-trans-4-propylcyclohexylphenoxy)-hexane
1-(tri-(1-methyl-3-oxo-but-1-enyloxy)-silyl)-3-(p-trans-4-propylcyclohexylphenoxy)-propane.

FORMULATION EXAMPLE A

A mixture of
50.2% p-trans-4-propylcyclohexyl-phenyl butyrate
25.3% trans-4-propylcyclohexyl p-trans-4-butylcyclohexylbenzoate
24.3.% trans-4-propylcyclohexyl p-trans-4-propylcyclohexylbenzoate and
0.2% of 1-triethoxysilyl-3-(p-trans-4-propylcyclohexylphenoxy)-propane
is suitable as a liquid crystal dielectric.

FORMULATION EXAMPLE B

A mixture of
51.8% of p-trans-4-propylcyclohexyl-phenyl butyrate
26.0% of trans-4-propylcyclohexyl p-trans-4-butylcyclohexylbenzoate
22.1% of trans-4-propylcyclohexyl p-trans-4-propylcyclohexylbenzoate and
0.1% of 1-triecetoxysilyl-3-(p-trans-4-propylcyclohexylphenoxy)-propane
is suitable as a liquid crystal dielectric.

USE EXAMPLE I

Coating of glass surfaces

The pieces of glass thoroughly cleaned in 1,1,1-trichloroethane vapor are printed with a 0.5% solution of 1-triethoxysilyl-3-(p-trans-4-propylcyclohexylphenoxy)-propane in isopropanol and the solvent is evaporated off in air. Introducing the printed pieces of glass into a steam-containing atmosphere for a short time increases the stability of the orientation layer. Use Example II: Coating of glass surfaces The pieces of glass thoroughly cleaned in 1,1,1-trichloroethane vapor are wetted with a 0.5% solution of 1-trichlorosilyl-3-(p-trans-4-propylcyclohexylphenoxy)-propane in 1,1,1-trichloroethane and the solvent is evaporated off in air.

The orientation of liquid crystal phases on surfaces treated with compounds of the formula I is in all cases better than the orientation effected by the trialkanoylsilanes claimed in German Offenlegungsschrift No. 3,331,515.

The other organosilicon compounds of the formula I are equally suitable for coating surfaces for producing a homotropic orientation of liquid crystal phases.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. An organosilicon compound of the formula

$R^1-A^1-A^2-O-C_nH_{2n}-SiX_aY_bZ_c$ wherein
- $R^1$ is H, alkyl of 1-10 C atoms, alkyl of 1-10 C atoms wherein one or two non-adjacent $CH_2$ groups are replaced by 0 atoms, F, Cl, Br or CN,
- $A^1$ and $A^2$ are each independently 1, 4-phenylene (Phe) or 1,4cyclohexylene (Cy),
- X, Y and Z are each independently H, F, Cl, Br, I, CN, NC, OCN, NCO, SCN, NCS, $N_3$, alkoxy of 1 to 15 C atoms, 1-methyl-3-oxobut-1-enyloxy or alkoxy of 1-15 C atoms wherein one or more non-adjacent $CH_2$ groups are replaced by an oxo —O— atom or —CH=CH—,
- a, b and c are 0, 1, 2 or 3 and
- n is 2, 3, 4, 5 or 6, with the provisos that a+b+c+3, at least one of X, Y and Z is other than H and X, Y and Z are not all Cl.

2. A compound of claim 1 of formula $R^1-Phe-Phe-O-C_nH_{2n}-SiX_aY_bZ_c$.

3. A compound of claim 1 of the formula $R^1-Cy-Phe-O-C_nH_{2n}-SiX_aY_bZ_c$.

4. A compound of claim 1 of the formula $R^1Phe-Phe-O-C_nH_{2n}-SiX_aY_bZ_c$.

5. A compound of claim 1 of the formula $R^1-Cy-Cy-O-C_nH_{2n}-SiX_aY_bZ_c$.

6. A compound of claim 1 wherein $R^1$ is alkyl.

7. A compound of claim 1 wherein $R^1$ is alkoxy.

8. A compound of claim 1 wherein X, Y and Z are the same.

9. A compound of claim 1 wherein X, Y and Z are halogen or alkoxy.

10. A compound of claim 8 wherein X, Y and Z are methoxy, ethoxy, propyloxy, isopropyloxy or 1-methyl-3-oxobut-1-enyloxy.

11. A compound of claim 1 wherein n is 3.

12. A compound of claim 1 wherein at least one of $A^1$ and $A^2$ is trans-Cy.

13. A compound of claim 1 wherein $C_nH_2n$ is $-(CH_2)_3-$.

14. In a liquid crystal dielectric useful for electrooptical display elements and comprising at least two liquid crystal components, the improvement wherein the dielectric comprises a compound of claim 1.

15. A dielectric of claim 14 wherein the amount of said compound is 0.01 to 1%.

16. In an electrooptical display element comprising a liquid crystal phase, the improvement wherein the phase is a dielectric according to claim 14.

17. A surface coated with a compound of claim 1.

18. In an electrooptical display element comprising a liquid crystalline dielectric in contact with a surface, the improvement wherein the surface is coated with a compound of claim 1.

19. 1-triethoxysilyl-3-(p-trans-4-propylcyclohexylphenoxy)-propane, a compound of claim 1.

* * * * *